United States Patent [19]

Shirasaki et al.

[11] Patent Number: 5,661,150

[45] Date of Patent: Aug. 26, 1997

[54] DRUG FOR NEUROPROTECTION

[75] Inventors: Yasufumi Shirasaki; Hitoshi Yamaguchi, both of Tokyo, Japan

[73] Assignee: Daiichi Pharmaceutical Co., Ltd., Tokyo, Japan

[21] Appl. No.: 249,249

[22] Filed: May 25, 1994

[30] Foreign Application Priority Data

May 25, 1993 [JP] Japan .................... 5-122933

[51] Int. Cl.$^6$ .................. A61K 31/415; A61K 31/495
[52] U.S. Cl. .................. 514/252; 514/403; 514/406
[58] Field of Search .................. 514/252, 403, 514/406

[56] References Cited

PUBLICATIONS

Pohorecki, Roman et al., "Ketamine, MK–801 or Calmidazolium Protects Rat Hippocampal Energy Status During in Vitro Ischemia", *Ann. N. Y. Acad. Sci.*, vol. 625 (1991) pp. 818–820.

Zivin, Justin A. et al., "Phenothiazines reduce ischemic damage to the central nervous system", *Brain Res.*, vol. 482, No. 1, (1989) pp. 189–193.

Yu, Melvin J., Ph.D. et al., "A Phenothiazine Derivative Reduces Rat Brain Damage After Global or Focal Ischemia", *Stroke*, vol. 23, No. 9, (1992) pp. 1287–1291.

Seubert, P. et al., "Calmodulin Stimulates the Degradation of Brain Spectrin by Calpain", *Synapse*, vol. 1, No. 1, (1987) pp. 20–24.

Harris et al., J. Biol. Chem., vol. 264, No. 29, pp. 17401–17408. Oct. 15, 1989.

Kogure et al., Tanpakushitsu, Kakusan, Koso, vol. 35, pp. 1254–1271. 1990.

Hara et al., J. Cerebral Blood Flow and Metabolism, vol. 10, pp. 646–653. 1990.

*Primary Examiner*—Richard L. Raymond
*Attorney, Agent, or Firm*—Sughrue, Mion, Zinn, Macpeak & Seas

[57] ABSTRACT

A drug containing a calmodulin inhibitor as an active ingredient is disclosed. This drug is useful in the suppression of neuronal cell death, in particular brain neuronal cell death, due to, for example, cerebral ischemia.

Also, a drug containing a compound capable of inhibiting binding of calmodulin to a cytoskeltal protein as an active ingredient and a drug containing a compound suppressing the breakdown of a cytoskeltal protein as an active ingredient are disclosed.

These drugs are useful in the treatment and prevention of various diseases in the brain and sequelae thereof as well as in the prevention of relapses of these diseases.

9 Claims, No Drawings

DRUG FOR NEUROPROTECTION

FIELD OF THE INVENTION

This invention relates to a drug which is useful in the treatment and prevention of various diseases in the brain and sequelae thereof as well as in the prevention of relapses of these diseases.

BACKGROUND OF THE INVENTION

Cerebrovascular disorders (the term "cerebrovascular disorders" as used herein means disorders in various brain cells and intracerebral blood vessels induced by, for example, ischemia) break out due to so-called cerebral ischemia, wherein the blood stream in the brain is lowered to the threshold or below, which is induced by occlusion of blood vessel caused by a constriction of blood vessel, cerebral thrombosis or cerebral embolus. Kirino et al. [Brain Res., 377:344–347 (1982)]found out that when transient cerebral ischemia was loaded to a gerbil, so-called delayed neuronal cell death, i.e., slow and delayed hippocampal pyramidal neuronal cell death was observed 2 or 3 days thereafter. Although attempts have been made to clarify the degenerative process of neuron after central damage (for example, ischemia), this mechanism has not been clarified so far.

According to Siesjoe and Bengtsson [J. Cereb. Blood Flow Metab., 9:127 (1989)], at ischemia, glutamate is liberated from the presynaptic side to synaptic clefts and then binds to a glutamate receptor in the postsynaptic side. Thus the calcium ion influx into the cells and the liberation of calcium ion from intracellular storage sites are promoted. At the same time, the extrusion of intracellular calcium ion is suppressed due to decreased calcium-ATPase activity. As a result, the intracellular calcium ion concentration is elevated, which results in the neuronal cell death. Compared with the extracellular calcium ion concentration, the intracellular calcium ion concentration is extremely low. It is known that cells cannot survive when the intercellular calcium ion concentration is elevated to a certain level. However the process from an increase in the intracellular calcium ion concentration to neuronal cell death has not been clarified yet.

Also, there have been reported that at cerebral ischemia, calmodulin, which is a calcium-binding protein, was activated [Picone et al., J. Cereb. Blood Flow Metab., 9:805–811 (1989)], the activity of calmodulin-dependent protein kinase was changed [Churn et al., Stroke, 21:1715–1721 (1990)]and breakdown of fodrin, which is a calmodulin-binding cytoskeltal protein, was accelerated by cerebral ischemia disorders [Seubert et al., Brain Res., 492:366–370 (1989)].

On the other hand, there have been also reported that calmodulin accelerated the breakdown of fodrin by calpain [Harris et al., J. Biol. Chem., 264:17401–17408 (1989)]and trifluoropelazine, which is a compound having a calmodulin-inhibition effect, suppressed the breakdown of fodrin [Seubert et al., Synapse, 1:20–24 (1987)]. However it has never been reported that these phenomena participate in neuronal cell death.

Although it is considered that a drug having a calmodulin-inhibition effect might be applicable to antihypertensive drug, antianginal drug, antiarrhythmic drug, drug for treating schizophrenia or drug for improving cerebral circulation on the basis of vasodilator effect, no effect of suppressing neuronal cell damage has been proved so far. Kogure et al. reported that as a result of their examination, W-7, which is a substance having a calmodulin- inhibition effect, exhibited no effect of suppressing delayed neuronal cell death and thus denied the applicability of a calmodulin inhibitor as a drug for treating cerebrovascular disorders (Kogure et al., Tanpakushitsu, Kakusan, Koso, 35:1254 (1990)].

It has been reported that a phenothiazine compound, which also has an effect of inhibiting calmodulin, relieved cerebral ischemic disorders by its antioxidant effect [Ye et al., Stroke, 23:1287–1291 (1992)].

With the tendency toward an aging society in recent years, increases in brain disorders including cerebrovascular disorders and Alzheimer's disease have become a serious social problem. It is known that the root of these diseases lies in brain neuronal cell death caused by various factors. For example, cerebrovascular disorders are induced by cerebral ischemia and the severity of these diseases relates to the ischemic period. Slight ischemia brings about little problem, while prolonged ischemia results in irreversible damages in the brain. Since matured neurons are not regenerated through cell division any more, these disorders remain as permanent organic changes and strongly affect the prognosis.

Therefore, it is highly useful in treating cerebrovascular disorders and relieving the sequelae thereof to suppress neuronal cell death. Further, it has been proposed that neuronal cell death based on the accelerated degradation of cytoskeltal protein causes Alzheimer's disease. Accordingly, suppression of neuronal cell death is useful in the treatment and prevention of Alzheimer's disease and relief of the sequelae thereof too.

If the excessive activation of calmodulin induced by an increase in the intracellular calcium ion concentration at neuronal cell disorders can be suppressed by using a calmodulin inhibitor, therefore, neuronal cell death can be suppressed.

Delayed neuronal cell death occurs several days after the break out of cerebrovascular disorders. The present inventors have found out that the content of calmodulin in cytoplasm begins to decrease from the early stage (more concretely, even 1 hour after ischemia) while the calmodulin content in membrane fraction increases. This is the same phenomenon as the one observed when an excessive amount of calcium ion is added to a hippocampal homogenate. It indicates that calcium ion binds to calmodulin at cerebral ischemia and some part thereof translocates into the membrane side. The present inventors have further clarified that the degradation of fodrin, which is a cytoskeltal protein contained in the membrane, is accelerated by the addition of calcium ion and that calmodulin binds to the breakdown products.

The present inventors have further found out that in a cerebral ischemic model of gerbil, the breakdown of fodrin is accelerated prior to neuronal cell death. Thus they have examined compounds A and B, each having a high selectivity for calmodulin and an intense calmodulin inhibition effect, and consequently found out that these compounds suppress the translocation of calmodulin into the membrane in the early stage of cerebral ischemia, suppress the breakdown of fodrin and, in its turn, suppress neuronal cell death. The present invention has been thus completed.

SUMMARY OF THE INVENTION

Accordingly, the present invention relates to a drug for neuroprotection which is characterized by containing a calmodulin inhibitor as an active ingredient.

Further, the present invention relates to a drug for suppressing brain cell death which is characterized by containing a calmodulin inhibitor as an active ingredient.

Further, the present invention relates to a drug for suppressing neuronal cell death which is characterized by containing a calmodulin inhibitor as an active ingredient.

Further, the present invention relates to a drug for suppressing brain neuronal cell death which is characterized by containing a calmodulin inhibitor as an active ingredient.

Further, the present invention relates to a drug for neuroprotection at cerebral ischemia which is characterized by containing a calmodulin inhibitor as an active ingredient.

Further, the present invention relates to a drug for suppressing brain cell death at cerebral ischemia which is characterized by containing a calmodulin inhibitor as an active ingredient.

Further, the present invention relates to a drug for suppressing neuronal cell death at cerebral ischemia which is characterized by containing a calmodulin inhibitor as an active ingredient.

Further, the present invention relates to a drug for suppressing brain neuronal cell death at cerebral ischemia which is characterized by containing a calmodulin inhibitor as an active ingredient.

Further, the present invention relates to a drug for neuroprotection which is characterized by containing a compound inhibiting binding of calmodulin to a cytoskeltal protein as an active ingredient.

Further, the present invention relates to a drug for suppressing brain cell death which is characterized by containing a compound inhibiting binding of calmodulin to a cytoskeltal protein as an active ingredient.

Further, the present invention relates to a drug for suppressing neuronal cell death which is characterized by containing a compound inhibiting binding of calmodulin to a cytoskeltal protein as an active ingredient.

Further, the present invention relates to a drug for suppressing brain neuronal cell death which is characterized by containing a compound inhibiting binding of calmodulin to a cytoskeltal protein as an active ingredient.

Further, the present invention relates to a drug for neuroprotection at cerebral ischemia which is characterized by containing a compound inhibiting binding of calmodulin to a cytoskeltal protein as an active ingredient.

Further, the present invention relates to a drug for suppressing brain cell death at cerebral ischemia which is characterized by containing a compound inhibiting binding of calmodulin to a cytoskeltal protein as an active ingredient.

Further, the present invention relates to a drug for suppressing neuronal cell death at cerebral ischemia which is characterized by containing a compound inhibiting binding of calmodulin to a cytoskeltal protein as an active ingredient.

Further, the present invention relates to a drug for suppressing brain neuronal cell death at cerebral ischemia which is characterized by containing a compound inhibiting binding of calmodulin to a cytoskeltal protein as an active ingredient.

Further, the present invention relates to a drug for neuroprotection which is characterized by containing a compound suppressing the breakdown of a cytoskeltal protein as an active ingredient.

Further, the present invention relates to a drug for suppressing brain cell death which is characterized by containing a compound suppressing the breakdown of a cytoskeltal protein as an active ingredient.

Further, the present invention relates to a drug for suppressing neuronal cell death which is characterized by containing a compound suppressing the breakdown of a cytoskeltal protein as an active ingredient.

Further, the present invention relates to a drug for suppressing brain neuronal cell death which is characterized by containing a compound suppressing the breakdown of a cytoskeltal protein as an active ingredient.

Further, the present invention relates to a drug for neuroprotection at cerebral ischemia which is characterized by containing a compound suppressing the breakdown of a cytoskeltal protein as an active ingredient.

Further, the present invention relates to a drug for suppressing brain cell death at cerebral ischemia which is characterized by containing a compound suppressing the breakdown of a cytoskeltal protein as an active ingredient.

Further, the present invention relates to a drug for suppressing neuronal cell death at cerebral ischemia which is characterized by containing a compound suppressing the breakdown of a cytoskeltal protein as an active ingredient.

Further, the present invention relates to a drug for suppressing brain neuronal cell death at cerebral ischemia which is characterized by containing a compound suppressing the breakdown of a cytoskeltal protein as an active ingredient.

The term "a drug for neuropretection" as used herein means a drug which is to be used in order to suppress neuronal cell death to thereby prevent, relieve or treat various disorders in cerebral functions caused by this neuronal cell death.

DETAILED DESCRIPTION OF THE INVENTION

It has been considered that calmodulin inhibitors would be applicable to drugs for treating diseases in circulatory organs such as antihypertensive drug, antianginal drug, antiarrhythmic drug, and drug for improving cerebral circulation or psychotropic drug. However, the findings of the present inventors reveal that a calmodulin inhibitor is usable as a drug for treating cerebrovascular disorders. That is to say, a calmodulin inhibitor is highly useful as a drug for treating various diseases induced by the excessive activation of calmodulin. In particular, it is highly useful as a drug for treating or preventing cerebrovascular disorders (for example, cerebral infarction, cerebral embolus, transient cerebral ischemia, cerebral thrombosis), cerebral denaturation diseases (for example, Alzheimer's disease, Parkinson's disease) and other cerebral disorders (for example, drug addiction, gas poisoning, trauma cerebral diseases), and diseases induced thereby (for example, depressed voluntariness, depression and disorders in memory).

As a matter of course, the present invention involves methods for treating various diseases induced by the excessive activation of calmodulin which are characterized by administering a calmodulin inhibitor.

The drug for neuroprotection of the present invention may be administered either orally or parenterally.

The dose of the drug for neuroprotection of the present invention can be appropriately varied depending on the conditions, age, body weight and severity of the patient. In the case of oral administration, it can be administered to an adult in a dose of from 1 mg to 1000 mg, preferably from 10 mg to 500 mg, per day. It may be administered either at once or in several portions. As examples of the administration form, tablets, capsules, dusts and granules may be cited. These preparations can be produced by a publicly known method with the use of additives which are commonly employed in the art, for example, excipients, lubricants and binders.

In the case of parenteral administration, it can be administered to an adult in a dose of from 1 mg to 500 mg, preferably from 10 mg to 200 mg, per day. As preferable administration routes, subcutaneous intravenous injection and intravenous drip infusion may be cited.

The drug for neuroprotection of the present invention can be formulated into a preparation by a widely known method. Now a formulation with the use of the compound B employed in the experiments described herein will be given by way of example. [Formulation Example 1]

| (1) compound B | 10 g |
|---|---|
| (2) lactose | 50 g |
| (3) corn starch | 15 g |
| (4) hydroxypropylcellulose | 8 g |
| (5) carboxymethylstarch sodium | 7 g |
| (6) magnesium stearate | 1 g |

The above-mentioned components (1), (2), (3) and (5) are homogeneously mixed in a fluidized bed granulating machine and granulated by using a 6% aqueous solution of the component (4) as a binder. Then the component (5) is added thereto and homogeneously mixed to thereby give a powder to be tabletted. Next, the powder was formulated into 100 tablets of 8 mm in diameter each containing 100 mg of the component (1). [Formulation Example 2]

| (1) compound B | 2 g |
|---|---|
| (2) 0.1 N hydrochloric acid | 150 ml |
| (3) glucose | 50 g |
| (4) distilled water for injection. | |

The above-mentioned components (1), (2) and (3) are mixed together and the distilled water for injection was further added thereto so as to adjust the total volume to 1000 ml. The solution thus obtained was sterilely filtered through a 0.2 μm filter and pipetted in 10 ml portions into 10 ml ampuls.

It is expected that the drug for neuroprotection of the present invention would exert additional or multiplier effects of treating or preventing various diseases when combined with other drugs. Examples of such drugs include those for improving cerebral circulation (for example, cinepazide maleate), drugs for improving cerebral metabolism (for example, idebenone, indeloxazine), psychotropics (for example, timiperone, imipramine, diazepam), drugs for lowering intracranial pressure (for example, glyceol), antihypertensive drugs, vasodilators (for example, trapidil), antipyretic analgesics, antiinflammatory steroids, antiplatelets (for example, ticlopidine), anticoagulants (for example, heparin), fibrinolytic drugs (for example, tissue plasminogen activator), diuretics, antihyperlipemia (for example, probucol), drugs for treating digestive ulcer, blood substituents, drugs for hepatic diseases and drugs for malignant tumor.

To further illustrate the present invention in greater detail, and not by way of limitation, the following Examples will be given.

[Pharmacological Example 1]Calmodulin Inhibition Effect

The calmodulin inhibition effect of a compound was evaluated by using its effect of inhibiting calmodulin-depending phosphodiesterase (PDE) as an index. The experiment was performed by modifying the method of Thompson et al. [Advances in Cyclic Nucleotide Research, 10, 69 (1979)]. Namely, 50 mM tris buffer (pH 7.5, containing 5 mM $MgCl_2$, and 1 mg/ml of bovine serum albumin), 1 mM $CaCl_2$, [$^3H$]-cGMP, calmodulin (CAM, from bovine brain), CaM-PDE (calmodulin-depending phosphodiesterase, from bovine brain) and a specimen were mixed together and incubated at 30° C. for 10 minutes. After ceasing the reaction by heating in a boiling water bath for 1 minute, snake venom (1 mg/ml) was added thereto and the resulting mixture was reacted at 30° C. for 10 minutes to thereby convert 5'-GMP formed by PDE into guanosine. Next, the unreacted cGMP was adsorbed by an ion exchange resin (AGI-X8). Subsequently, the mixture was centrifuged and the radioactivity of the supernatant was measured with a liquid scintillation counter. The inhibition effects (expressed in $IC_{50}$) of the employed compounds A and B thus determined were respectively 3.93 μM and 5.46 μM. On the other hand, the $IC_{50}$ of W-7 employed as a control compound was 33.5 μM.

[Pharmacological Example 2]Effect on Intracellular Localization of Hippocampal Calmodulin The hippocampus of a gerbil was homogenized with 20 mM tris buffer (pH 7.5) containing 0.1 mM leupeptin, 0.1 mM PMSF and 0.01 mg/ml of aprotinin. After adding a 1 mM aqueous solution of calcium chloride or 1 mM EGTA [ethylene-bis(oxyethylenenitrylo)tetraacetic acid, [—$CH_2OCH_2CH_2N$—$(CH_2COOH)_2]_2$], it was incubated at 37° C. for 30 minutes. The homogenate was centrifuged at 100,000×g to thereby separate into a supernatant (a soluble fraction) and a precipitate (a membrane fraction). The precipitate was solubilized with 0.1% Lubrol PX. Then the calmodulin contents in the soluble fraction and the membrane fraction were determined by radioimmunoassay. The calmodulin content in the soluble fraction was significantly decreased by adding the aqueous solution of calcium chloride to the hippocampal homogenate, compared with the one treated with EGTA. On the contrary, the content of calmodulin in the membrane fraction was increased by adding the aqueous solution of calcium chloride. The compound A (10 μM) significantly suppressed the change in calmodulin content caused by calcium ion. Table 1 shows the results.

On the other hand, W-7 and the compound A exerted no effect on the behavior of calmodulin in the presence of EGTA.

TABLE 1

Effect on intracellular localization of calmodulin in hippocampus (1)

| Test Group | Calmodulin Content (μg/mg protein) | |
|---|---|---|
| | Soluble Fraction | Membrane Fraction |
| Control | 4.5 ± 0.13 | 8.8 ± 0.25 |
| 1 mM EGTA | 12.3 ± 0.77** | 7.6 ± 0.40 |
| 1 mM $CaCl_2$ | 0.83 ± 0.04** | 11.4 ± 0.34** |
| 1 mM $CaCl_2$ + 10 μM compound A | 1.75 ± 0.52**# | 7.1 ± 0.50# |

**: $P < 0.01$ vs. control.
: $P < 0.05$ vs. 1 mM $CaCl_2$.

Both common carotid arteries of a gerbil were ligated for 10 minutes. One hour and 24 hours after allowing the blood stream to flow again, the calmodulin content in the hippocampus was determined by radioimmunoassay. The compound A (100 mg/kg) was suspended in 0.5% methylcellulose and orally administered to the animal 1 hour before cerebral ischemia. The content of calmodulin in the cytoplasm (the soluble fraction) was significantly decreased 1 hour after cerebral ischemia, while the calmodulin content in the membrane fraction was increased on the contrary (Test 1). 24 hours after cerebral ischemia, an increase in the calmodulin content was observed in the membrane fraction. However, the compound A significantly suppressed such an increase in the calmodulin content in the membrane fraction (Test 2). Table 2 shows the results.

TABLE 2

Effect on intracellular localization of calmodulin in hippocampus (2)

| Test Group | Calmodulin Content (μg/mg protein) | |
|---|---|---|
| | Cytoplasm Fraction | Membrane Fraction |
| Test 1: | | |
| Normal | 2.1 ± 0.12 | 2.1 ± 0.10 |
| Cerebral ischemia (after 1 hr) | 1.7 ± 0.08* | 2.7 ± 0.22* |
| Test 2: | | |
| Normal | 1.0 ± 0.06 | 1.3 ± 0.10 |
| Cerebral ischemia (after 24 hrs) | 1.1 ± 0.05 | 1.9 ± 0.10** |
| Cerebral ischemia + compound A (100 mg/kg) | 1.3 ± 0.08 | 1.4 ± 0.05 |

*: P < 0.05.
**: P < 0.01 vs. normal group.
n = 10–12.

These pharmacological examples indicate the change in localization of calmodulin in the cells at the early stage of cerebral ischemia. Such a change was similar to the one induced by adding calcium ion to a hippocampal homogenate. Further, the compound A, which exerts a strong effect of inhibiting calmodulin, suppressed the change in the localization of calmodulin in cells under the addition of calcium ion (in vitro) and in the cerebral ischemic model.

[Pharmacological Example 3]Effect of Calcium Ion on Breakdown of Cytoskeltal Protein Fodrin The hippocampus taken out from a gerbil was homogenized with 20 mM tris buffer (pH 7.5). After adding 1 mM $CaCl_2$ or 1 mM EGTA, it was incubated at 37° C. for 1 hour. Then the homogenate was centrifuged at 10,000×g for 30 minutes. After separating proteins contained in the supernatant fraction by SDS-PAGE, the proteins were identified by western blotting with the use of a fodrin antibody (rabbit anti α-Spectrin) and a calmodulin antibody (sheep anti-bovine calmodulin). Under the EGTA-treatment, stable breakdown products of fodrin (140–150 kDa) were little observed. When $Ca^{++}$ was added, however, bands of the breakdown products appeared. As the result of the western blotting of calmodulin, bands assignable to calmodulin were observed almost at the same positions of those assignable to fodrin and fodrin breakdown products, which indicates that calmodulin bound not only to fodrin but also to breakdown products thereof.

[Pharmacological Example 4]Change in Fodrin in Cerebral Ischemic Model

Both common carotid arteries of a gerbil were ligated for 10 minutes to thereby prepare a cerebral ischemic model. Four, 24 and 48 hours after allowing the blood stream to flow again, the hippocampus was taken out and homogenized with 20 mM tris buffer (pH 7.5) containing 0.1 mM leupeptin, 0.1 mM PMSF and 0.15 mM aprotinin. After centrifuging at 10,000×g for 30 minutes, proteins in the supernatant were separated by SDS-PAGE. Then fodrin and breakdown products thereof were identified by the same method as the one described in Pharmacological Example 3. The compound B (100 mg/kg) was administered 1 hour before cerebral ischemia and evaluated 48 hours thereafter. Fodrin breakdown products were little detected from the normal gerbil. In the case of the cerebral ischemic model, on the other hand, breakdown products appeared 4 hours after allowing the blood stream to flow again and similar bands were observed after 48 hours. These fodrin breakdown products due to cerebral ischemia were scarcely detected under the treatment with the compound B having a strong calmodulin inhibition effect.

[Pharmacological Experiment 5]Change in Hippocampal Neuronal Cells in Cerebral Ischemic Model When transient cerebral ischemia was loaded to a gerbil, necrosis of hippocampal cells was observed from several days thereafter. This change is called delayed neuronal cell death. Cerebral ischemia was loaded to a gerbil for 5 minutes. Seven days thereafter, the animal was sacrificed and the neuronal cells remaining in the hippocampal CA1 region were counted. Most of the hippocampal CA1 cells died due to the cerebral ischemia. When the compound A or B (100 mg/kg) was orally administered to the animal 1 hour after cerebral ischemia, a protective effect on neuronal cells was clearly observed. Table 3 shows the results.

TABLE 3

Change in hippocampal neuronal cells in cerebral ischemic model

| | Hippocampal Neuronal Cell Density (/mm) |
|---|---|
| Normal | 194 ± 6.1 |
| Cerebral ischemia | 9 ± 1.3 |
| Cerebral ischemia + compound A | 98 ± 22.0** |
| Cerebral ischemia + compound B | 131 ± 21.2** |

**: P < 0.01 vs. cerebral ischemia group.
n = 9–10.

[Referential Example 1]Ethyl 5,6-dimethoxy-1-(3,4-dimethoxy-benzyl)-1H-indazole-3-carboxylate Ethyl 5,6-dimethoxy-1H-indazole-3-carboxylate (250.2 g) was suspended in dimethyl sulfoxide (5000 ml, dried with Molecular Sieve 4A). Then lithium methoxide (38.0 g) was added thereto and the mixture was stirred at room temperature. After stirring at room temperature for 1 hour, 3,4-dimethoxybenzyl chloride (185.6 g) [prepared from 336.4 g of 3,4-dimethoxybenzyl alcohol, 300 ml of conc. hydrochloric acid and 500 ml of diethyl ether]was added dropwise to the mixture at room temperature within 10 minutes. Then the mixture was stirred at room temperature for 1 hour. After adding 3,4-dimethoxybenzyl chloride (55.6 g), the mixture was stirred at room temperature for 1 hour. Further, 3,4-dimethoxybenzyl chloride (55.6 g) was added and the mixture was stirred at room temperature for additional 1 hour. The reaction mixture was poured into ice-water (30000 ml) with stirring. The supernatant was removed by decantation and a residue was dissolved in chloroform (10000 ml), dried over sodium sulfate, filtered and evaporated under reduced pressure. The residue (497.0 g) thus obtained was separated and purified by using silica gel columns (chloroform/carbon tetrachloride/ethyl acetate =5/5/1, silica gel 2 kg×9, followed by ethyl acetate/hexane =2/1, silica gel 2 kg×4). The obtained eluate was recrystallized from ethyl acetate. Thus 205.0 g of ethyl 5,6-dimethoxy-1-(3,4-dimethoxybenzyl)-1H-indazole-3-carboxylate (m.p.: 138°–141° C.) was obtained in the form of prism crystals.

IR (KBr)cm$^{-1}$: 1728, 1496, 1266, 1216, 1204, 1138, 1022.

$^1$H-NMRδ (ppm, CDCl$_3$): 1.49 (3H, t, J=6.8 Hz), 3.78 (3H, s), 3.85 (6H, s), 3.95 (3H, s), 4.53 (2H, q, J=6.8 Hz), 5.58 (2H, s), 6.63 (1H, s), 6.76 (1H, s), 6.80 (2H, s), 7.56 (1H, s).

Elemental analysis: Calcd. for $C_{21}H_{24}N_2O_6$: C, 62.99%; H, 6.04%; N, 7.00%. Found: C, 62.83%; H, 5.99%; N, 6.93%.

[Referential Example 2] 5,6-Dimethoxy-1-(3,4-dimethoxy-benzyl)-1H-indazole-3-methanol 5,6-Dimethoxy-1-(3,4-dimethoxybenzyl)-1H-indazole-3-carboxylate (205.0 g) was ground in a mortar and suspended in tetrahydrofuran (1500 ml) at room temperature. Then sodium borohydride (96.8 g) was added thereto and the mixture was stirred at room temperature. Methanol (300 ml) was slowly added dropwise thereinto within 30 minutes. After the completion of the addition, the reaction mixture was heated to 50° C. and stirred for 5 hours. After adding sodium borohydride (19.4 g) and methanol (60 ml), the mixture was stirred at room temperature overnight. Then the reaction mixture was added in portions into a mixture of conc. hydrochloric acid (200 ml), water (5000 ml) and ice (1 kg) under stirring (pH 1–2). To this aqueous layer, a saturated aqueous solution of sodium bicarbonate was added with stirring at room temperature until the pH became about 8. As a result, a colorless solid was precipitated. This precipitate was collected by filtration, washed with water (500 ml×2), dissolved in chloroform (10000 ml), dried over sodium sulfate, filtered and the solvent was evaporated under reduced pressure. Thus a colorless solid (185.2 g) was obtained. This solid product was used in the subsequent reaction without purification.

Separately, a small amount of the solid product was taken and recrystallized from ethanol to give colorless prism crystals (m.p.: 187°×188° C.).

IR (KBr)cm$^{-1}$: 3272, 1520, 1470, 1438, 1418, 1318, 1284, 1256, 1210, 1166, 1140, 1062, 1026, 870, 834.

$^1$H-NMRδ (ppm, CDCl$_3$): 3.77 (3H, s), 3.82 (3H, s), 3.87 (3H, s), 3.92 (3H, s), 4.97 (2H, s), 5.40 (2H, s), 6.62 (1H, s), 6.69 (1H, m), 6.75 (2H, m), 7.13 (1H, s).

[Referential Example 3] 3-Chloromethyl-5,6-dimethoxy-1-(3,4-dimethoxybenzyl)-1H-indazole 5,6-Dimethoxy-1-(3,4-dimethoxybenzyl)-3-hydroxymethyl-1H-indazole (184.0 g) was dissolved in dichloromethane (1500 ml) at room temperature. After the dissolution, the reaction mixture was ice-cooled and stirred. Then thionyl chloride (75.4 ml) was dropped thereinto within 20 minutes. The reaction mixture was stirred at room temperature and dichloromethane (3500 ml) was added thereto. Then it was washed with a saturated aqueous solution of sodium bicarbonate (1000 ml), dried over sodium sulfate, filtered and the solvent was evaporated under reduced pressure. Thus 189.7.g of a colorless solid was obtained. This solid product was used in the subsequent reaction without purification.

$^1$H-NMRδ (ppm, CDCl$_3$): 3.78 (3H, s), 3.84 (3H, s), 3.88 (3H, s), 3.95 (3H, s), 4.95 (2H, s), 5.44 (2H, s), 6.65 (1H, s), 6.71 (3H, m), 7.10 (1H, s).

[Referential Example 4] 5,6-Dimethoxy-1-(3,4-dimethoxy-benzyl)-1H-indazole-3-acetonitrile 3-Chloromethyl-5,6-dimethoxy-1-(3,4-dimethoxybenzyl)-1H-indazole (187.0 g) was dissolved in dimethyl sulfoxide (1000 ml) and a solution was stirred at room temperature. Then sodium cyanide (134.0 g) which had been ground in a mortar was added thereto. The reaction mixture was stirred at 50° C. for 2 hours. The reaction mixture was returned to room temperature, poured into water (15000 ml) and stirred for 1 hour. The solid thus precipitated was collected by filtration, washed with water (1000 ml×3), dissolved in chloroform (5000 ml), dried over sodium sulfate, filtered and evaporated under reduced pressure. The residue thus obtained was purified by using silica gel columns (chloroform/ethanol =50/1, silica gel 2 kg, followed by silica gel 2 kg, ethyl acetate/hexane =3:1) to give 111.0 g of a pale brown solid product. This solid product was used in the subsequent reaction without purification.

$^1$H-NMRδ (ppm, CDCl$_3$): 3.80 (3H, s), 3.84 (3H, s), 3.89 (3H, s), 3.94 (3H, s), 4.02 (2H, s), 5.43 (2H, s), 6.66 (1H, s), 6.72 (2H, m), 6.69 (1H, m), 7.06 (1H, m).

[Referential Example 5] 5,6-Dimethoxy-1(3,4-dimethoxy-benzyl)-1H-indazole-3-acetic acid 5,6-Dimethoxy-1-(3,4-dimethoxybenzyl)-1H-indazole-3-acetonitrile (111.0 g) was suspended in ethanol (1000 ml) at room temperature with stirring. Then a 10N aqueous solution of sodium hydroxide was added thereto and the mixture was heated under reflux for 2 hours. The reaction mixture was returned to room temperature and the ethanol (about 1000 ml) was evaporated under reduced pressure. Then water (2000 ml) was added thereto and the mixture was stirred overnight. After filtering off the insoluble matters, ether (500 ml) was added and materials soluble in the organic solvent was removed by discarding the organic layer. The aqueous layer was adjusted to pH 4 to 5 by adding conc. hydrochloric acid. Thus a solid was precipitated. This precipitate was collected by filtration and fractionally recrystallized from ethanol. Thus 41.0 g of 5,6-dimethoxy-1-(3,4-dimethoxy-benzyl)-1H-indazole-3-acetic acid was obtained. This product was used in the subsequent reaction without further purification.

$^1$H-NMRδ (ppm, CDCl$_3$): 3.77 (3H, s), 3.84 (3H, s), 3.88 (3H, s), 3.91 (3H, s), 4.03 (2H, s), 5.44 (2H, s), 6.64 (1H, s), 6.72 (2H, m), 6.77 (1H, m), 6.96 (1H, s).

[Referential Example 6] 1-((5,6-dimethoxy-1-(3,4-dimethoxy-benzyl)-1H-indazol-3-yl)acetyl]-4-(3-chloro-2-methylphenyl)-piperazine 5,6-dimethoxy-1-(3,4-dimethoxybenzyl)-1H-indazole-3-acetic acid (41.0 g) was suspended in dichloromethane (500 ml). Then 2,2-dipyridyl disulfide (24.5 g) and triphenylphosphine (30.0 g) were added thereto and the mixture was stirred at room temperature. Next, (3-chloro-2-methylphenyl)piperazine (23.5 g) dissolved in dichloromethane (200 ml) was dropped thereinto within 5 minutes and the mixture was stirred at room temperature for 30 minutes. Then dichloromethane (1000 ml) was added to the reaction mixture. After washing with water, the organic layer was dried over sodium sulfate, filtered and evaporated under reduced pressure. The residue thus obtained was purified by using a silica gel column (ethyl acetate/hexane=2/1, silica gel 2 kg) to give 61.5 g of a colorless solid. This solid product was used in the subsequent reaction without purification. A small amount of this product was taken and recrystallized from ethanol. Thus colorless prism crystals (m.p.: 165°–169° C.) were obtained.

IR(KBr)cm$^{-1}$: 1652, 1516, 1264, 1236.

$^1$H-NMRδ(ppm, CDCl$_3$): 1.24 (1.5H, t, J=7.3 Hz, Me of EtOH), 1.65 (4H, s), 2.55 (2H, m), 2.75 (2H, m), 3.72 (1H, m, CH$_2$ of EtOH), 3.76 (3H, s), 3.78 (3H, s), 3.89 (3H, s), 3.94 (3H, s), 4.09 (2H, s), 5.41 (2H, s), 6.65 (1H, s), 6.69 (2H, m), 6.73 (1H, s), 7.03 (1H, t, J=7.8 Hz), 7.09 (1H, d, J=6.8 Hz), 7.19 (1H, s).

[Referential Example 7]3-(2-(4-(3-chloro-2-methylphenyl)-1-piperazinyl)ethyl)-5,6-dimethoxy-1-(3,4-dimethoxybenzyl)-1H-indazole (compound 1-((5,6-Dimethoxy-1-(3,4-dimethoxybenzyl)-1H-indazol-3-yl)acetyl)-4-(3-chloro-2-methylphenyl)piperazine (60.5 g) was suspended in tetrahydrofuran (1000 ml). Then 1.0 mol-borane tetrahydrofuran complex tetrahydrofuran solution (500 ml) was added thereto and the mixture was heated under reflux for 2 hours. The reaction mixture was cooled to room temperature and water (30 ml) was added to thereby decompose the excessive reagent. After evaporation of the tetrahydrofuran under reduced pressure, conc. hydrochloric acid (300 ml) was added and the mixture was stirred at 50° C. for 1 hour. The aqueous layer was returned to room temperature and made alkaline with potassium carbonate. Then it was extracted with chloroform (3000 ml) and the organic layer was dried over sodium sulfate, filtered and evaporated under reduced pressure. The residue thus obtained was purified by using a silica gel column (chloroform/ethanol=40/1). Thus a colorless solid (50.0 g) was obtained. This product was recrystallized from ethanol to give 46.3 g of colorless prism crystals (m.p.: 148°–150° C.)

IR(KBr)cm$^1$: 1518, 1466, 1454, 1260, 1236, 1140, 1022, 1004.

$^1$H-NMRδ (ppm, CDCl$_3$): 2.35 (3H, s), 2.85 (2H, m), 3.02 (4H, m), 3.26 (2H, m), 3.78 (H, s), 3.83 (3H, s), 3.87 (3H, s), 3.94 (3H, s), 5.43 (2H, s), 6.62 (1H, s), 6.72 (2H, s), 6.78-(1H, m), 6.96 (1H, m), 7.11 (3H, m).

Elemental analysis: calcd. for C$_{31}$H$_{37}$N$_4$O$_4$Cl: C, 65.89%; H, 6.60%; N, 9.91%; Cl, 6.27%. found: C, 65.65%; H, 6.59%; N, 9.58%; Cl, 6.36%.

[Referential Example 8]5,6-Dimethoxy-1-(1-trityl-4-imidazolyl)methyl-1H-indazole-3-methanol Ethyl 5,6-dimethoxy-1-(1-trityl-4-imidazolyl)methyl)-1H-indazole-3-carboxylate (222.0 g), which had been ground in a mortar, was suspended in tetrahydrofuran (1300 ml) at room temperature and cooled with ice/water. Next, sodium bis-methoxyethoxy aluminum hydride (3.4 M toluene solution, ca. 250.0 ml) was added thereto within 15 minutes and cooled with ice/water under stirringm for 30 minutes. A persaturated aqueous solution of sodium sulfate was added to the reaction mixture and stirred for 1 hour. Then sodium sulfate was added thereto and the mixture was filtered. The sodium sulfate on the filter was washed with hot chloroform (500 ml ×5). After concentrating the filtrate, a colorless solid (220.1 g) was obtained. This product was recrystallized from chloroform to give 181.0 g of colorless prism crystals [m.p.: 115°–120° C. (dec.)].

IR(KBr)cm$^{-1}$: 3216, 3172, 3008, 2936, 1510, 1488, 1472, 1444,1302, 1260, 1172, 1156, 1128, 1102, 1036, 1014, 836, 764, 746, 702, 678, 666, 636.

$^1$H-NMRδ (ppm, CDCl$^3$): 3.91 (3H, s), 3.92 (3H, s), 4.92 (2H, s), 5.44 (2H, s), 6.76 (1H, s), 6.95 (1H, s), 7.05 (5H, m), 7.26 (1H, s, CHCl$_3$), 7.28 (1H, s), 7.31 (10H, m), 7.46 (1H, s).

Elemental analysis: Calcd. for C$_{33}$H$_{30}$N$_4$O$_3$·CHCl$_3$: C, 62.83; H, 4.81; N, 8.62. Found: C, 62.50; H, 4.63; N, 8.42.

[Referential Example 9]3-Chloromethyl-5,6-dimethoxy-1-[1-trityl-4-imidazolyl)methyl-1H-indazole 5,6-Dimethoxy-1(1-trityl-4-imidazolyl)methyl-1H-indazole-3-methanol (180.0 g), which had been ground in a mortar, was suspended in dichloromethane (1700 ml) at room temperature and then cooled with ice/water. Next, thionyl chloride (48.6 ml) was dropped thereinto within 5 minutes. The reaction mixture was poured into a saturated aqueous solution of sodium bicarbonate (2000 ml) and extracted with chloroform (5000 ml). After drying over sodium sulfate, filtering and evaporating under reduced pressure, a colorless solid was obtained (165.1 g). This solid product was used in the subsequent reaction without purification.

$^1$H-NMRδ (ppm, CDCl$_3$): 3.95 (3H, s), 4.09 (3H, s), 4.83 (2H, s), 5.67 (2H, s), 7.02 (8H, m), 7.37 (10H, m),.7.88 (1H, br).

[Referential Example 10]5,6-Dimethoxy-1(1-trityl-4-imidazolyl)methyl-1H-indazole-3-acetonitrile 3-Chloromethyl-5,6-dimethoxy-1(1-trityl-4-imidazolyl)methyl-1H-indazole (165.0 g) was suspended in dimethyl sulfoxide (1200 ml) and the solution was stirred at room temperature. Then potassium cyanide (43.6 g), which had been ground in a mortar, was added thereto. After stirring at 70° C. for 1 hour, the reaction mixture became homogeneous and transparent. The reaction mixture was returned to room temperature and poured into water (15000 ml) while vigorously stirring. The stirring was continued for 1 hour. The solid thus precipitated was collected by filtration, washed with water (1000 ml×3), dissolved in chloroform (5000 ml), dried over sodium sulfate, filtered and evaporated under reduced pressure. The residue thus obtained was purified by using a silica gel column (ethyl acetate) to give 108.7 g of a pale brown solid. This solid product was used in the subsequent reaction without purification.

$^1$H-NMRδ (ppm, CDCl$_3$): 3.92 (3H, s), 3.94 (3H, s), 3.97 (2H, s), 5.42 (2H, s), 6.79 (1H, s), 7.00 (1H, s), 7.02 (1H, s), 7.06 (5H, m), 7.30 (10H, m), 7.46 (1H, s).

[Referential Example 11]5,6-Dimethoxy-1(1-trityl-4-imidazolyl)methyl-1H-indazole-3-acetic acid 5,6-Dimethoxy-1(1-trityl-4-imidazolyl)methyl-1H-indazole-3-acetonitrile (107.0 g) was suspended in ethanol (1000 ml) at room temperature. Then a 10N aqueous solution of sodium hydroxide (prepared from 40.0 g of sodium hydroxide and 100 ml of water) was added thereto and the mixture was heated under reflux for 6 hours. The reaction mixture was returned to room temperature and poured into water (5000 ml). Then it was adjusted to pH 3 to 4 with a 10% aqueous solution of hydrochloric acid. As a result, a colorless solid was precipitated. Then it was filtered and washed with water (500 ml×3). The solid product thus obtained was dissolved in chloroform (5000 ml), dried over sodium sulfate, filtered and evaporated under reduced pressure. The solid product (134.0 g) thus obtained was used in the subsequent reaction without purification.

$^1$H-NMRδ (ppm, CDCl$_3$): 3.84 (3H, s), 3.87 (3H, s), 3.89 (2H, s), 5.43 (2H, s), 6.76 (1H, s), 6.88 (1H, s), 6.93 (1H, s), 7.03 (5H, m), 7.28 (10H, m), 7.48 (1H, s).

[Referential Example 12]4-(3-Chloro-2-methylphenol)-1((5,6-dimethoxy-1-(1-trityl-4-imidazolyl)methyl-1H-indazol-3-yl)acetyl) piperazine 5,6-Dimethoxy-1-(1-trityl-4-imidazolyl)methyl-1H-indazole-3-acetic acid (134.0 g) was suspended in dichloromethane (1000 ml). Then 2,2-dipyridyl disulfide (63.5 g) and triphenylphosphine (75.6 g) were added thereto and the mixture was stirred at room temperature (the suspension became transparent and homogeneous). Next, a solution of 4-(3-chloro-2-methylphenyl)piperazine (60.7 g) in dichloromethane (200 ml) was dropped thereinto within 5 minutes and the mixture was stirred at room temperature for 5 hours. The dichloromethane was evaporated from the reaction mixture under reduced pressure. To the residue, hot ethyl acetate was added and stirred. As a result, a solid was precipitated. Then it was colleated by filtration, washed with ethyl acetate (500 ml×2) and air-dried to give 140.4 g of a colorless solid. This solid product was purified by using a silica gel column (chloroform/ethanol=30/1) to give 134.9 g of a colorless solid. Next, it was recrystallized from ethanol to give 120.0 g of colorless prism crystals (m.p.: 103°–105° C.).

IR(KBr)cm$^{-1}$: 1646, 1628, 1508, 1466, 1450, 1430, 1260, 750, 702.

$^1$H-NMRδ (ppm, CDCl$_3$): 1.23 (1.2H, t, J=6.8 Hz, Me of EtOH), 2.28 (3H, s), 2.55 (2H, m), 2.73 (2H, m), 3.67 (4H, m), 3.71 (0.8H, q, J=6.8 Hz, CH$_2$ of EtOH), 3.90 (3H, s), 3.93 (3H, s), 4.03 (2H, s), 5.43 (2H, s), 6.68 (1H, s), 6.72 (1H, d, J=8.3 Hz), 6.90 (1H, s), 7.03 (7H, m), 7.14 (1H, s), 7.27 (10H, m), 7.41 (1H, s).

Elemental analysis: calcd. for C$_{45}$H$_{43}$ N$_6$O$_3$Cl·0.4EtOH H$_2$O: C, 70.10%; H, 5.70%; N, 10.70%; Cl, 4.72%. found: C, 70.02%; H, 5.78%; N, 10.60%; Cl, 5.11%.

[Referential Example 13]3-(2-(4-(3-Chloro-2-methylphenyl]-1-piperazinyl)ethyl)-5,6-dimethoxy-1 (4-imidazolylmethyl)-1H-indazole (compound B)

4-(3-chloro-2-methylphenyl)-1-((5,6-dimethoxy-1(1-trityl-4-imidazolyl)methyl)indazol-3-yl)acetyl)piperazine (120.0 g) was suspended in tetrahydrofuran (1000 ml). Then 1.0 M-borane tetrahydrofuran complex (800 ml) was added thereto and the mixture was heated under reflux for 90 minutes. The reaction mixture was cooled to room temperature and water (30 ml) was added to decompose the excessive reagent. After evaporating the tetrahydrofuran under reduced pressure, conc. hydrochloric acid (150 ml), water (200 ml) and ethanol (40 ml) were added and the mixture was stirred at 50° C. for 1 hour. The aqueous layer was stirred at room temperature and extracted with chloroform (3000 ml) which had been made alkaline with potassium carbonate. The organic layer was dried over sodium sulfate, filtered and distilled off under reduced pressure. The residue thus obtained was purified by silica gel column chromatography (chloroform/ethanol=40/1) to give a colorless solid product. It was recrystallized from isopropyl alcohol-isopropyl ether and thus 71.0 g of colorless prism crystals (m.p.: 143°–144.5° C.) were obtained.

IR(KBr)cm$^{-1}$: 1510, 1464, 1432, 1272, 1238, 1206, 1006.

$^1$H-NMRδ (ppm, CDCl$_3$): 2.34 (3H, s), 2.78 (4H, m), 2.90 (2H, m), 2.97 (4H, m), 3.17 (2H, m), 3.90 (3H, s), 3.91 (3H, s), 5.45 (2H, s), 6.83 (1H, s), 6.84 (1H, s), 6.92 (1H, m), 7.00 (1H, s), 7.09 (2H, m), 7.52 (1H, s).

Elemental analysis: calcd. for C$_{26}$H$_{31}$ N$_6$O$_2$Cl: C, 63.09%; H, 6.31%; N, 16.98%; Cl, 7.16%. found: C, 62.93%; H, 6.30%; N, 16.88%; Cl, 7.16%.

The present inventors have clarified that: 1) intracellular localization of calmodulin is changed by an increase in calcium ion concentration due to cerebral ischemia or addition of calcium ion; 2) activated calmodulin (calmodulin binding to calcium ion) translocates toward cell membrane and binds to fodrin, which is a protein lining the cell membrane, to thereby accelerate the breakdown of fodrin; and 3) the test compounds A and B, having strong effects compared with the existing calmodulin inhibitors, suppress neuronal cell death. That is to say, they have clarified that the activation of calmodulin and acceleration of breakdown of fodrin play important roles in neuronal cell death caused by cerebral ischemia. Therefore, a chemical capable of suppressing the abnormal activation of calmodulin is useful as a drug for neuronal damage.

While the invention has been described in detail and with reference to specific embodiments thereof, it will be apparent to one skilled in the art that various changes and modifications can be made therein without departing from the spirit and scope thereof.

What is claimed is:

1. A method of neuroprotection comprising administering to a subject in need of treatment a pharmaceutical composition comprising a calmodulin inhibitor in a neuroprotective amount and a pharmaceutically acceptable carrier, excipient or diluent.

2. A method for suppressing brain cell death comprising exposing brain cells to a pharmaceutical composition comprising a calmodulin inhibitor in an amount which suppresses brain cell death and a pharmaceutically acceptable carrier, excipient or diluent.

3. A method for suppressing neuronal cell death comprising exposing neuronal cells to a pharmaceutical composition comprising a calmodulin inhibitor in an amount which suppresses neuronal cell death and a pharmaceutically acceptable carrier, excipient or diluent.

4. A method for suppressing brain neuronal cell death comprising exposing brain neuronal cells to a pharmaceutical composition comprising a calmodulin inhibitor in an amount which suppresses brain neuronal cell death and a pharmaceutically acceptable carrier, excipient or diluent.

5. A method of neuroprotection at cerebral ischemia comprising administering to a subject with cerebral ischemia a pharmaceutical composition comprising a calmodulin inhibitor in an neuroprotective amount at cerebral ischemia and a pharmaceutically acceptable carrier, excipient or diluent.

6. A method for suppressing brain cell death at cerebral ischemia comprising administering to a subject with cerebral ischemia a pharmaceutical composition comprising a calmodulin inhibitor in an amount which suppresses brain cell death at cerebral ischemia and a pharmaceutically acceptable carrier, excipient or diluent.

7. A method for suppressing neuronal cell death at cerebral ischemia comprising administering to a subject with cerebral ischemia a pharmaceutical composition comprising a calmodulin inhibitor in an amount which suppresses neuronal cell death at cerebral ischemia and a pharmaceutically acceptable carrier, excipient or diluent.

8. A method for suppressing brain neuronal cell death at cerebral ischemia comprising administering to a subject with cerebral ischemia a pharmaceutical composition comprising a calmodulin inhibitor in an amount which suppresses brain neuronal cell death at cerebral ischemia and a pharmaceutically acceptable carrier, excipient or diluent.

9. The method of any one of claims 1–8 wherein said calmodulin inhibitor is 3-(2-(4-(3-chloro-2-methylphenyl)-1-piperazinyl)ethyl)-5,6-dimethoxy-1-(3,4-dimethoxybenzyl)-1H-indazole or 3-(2-(4-(3-chloro-2-methylphenyl)-1-piperazinyl)ethyl)-5,6-dimethoxy-1-(4-imidazolylmethyl)-1H-indazole.

* * * * *